United States Patent
Pandey et al.

(10) Patent No.: US 8,679,459 B2
(45) Date of Patent: Mar. 25, 2014

(54) B RING REDUCED-D RING OXIDIZED TETRAPYRROLIC PHOTOSENSITIZERS FOR PHOTODYNAMIC THERAPY AND TUMOR IMAGING

(75) Inventors: Ravindra K. Pandey, Williamsville, NY (US); Chao Liu, Barcelona (ES); Mahabeer Dobhal, Jaipur (IN); William Potter, Amherst, NY (US); Janet Morgan, Buffalo, NY (US); Allan Oseroff, Buffalo, NY (US); Stephanie Pincus, legal representative, Buffalo, NY (US)

(73) Assignee: Health Research, Inc., Buffalo, NY (US)

(*) Notice: Subject to any disclaimer, the term of this patent is extended or adjusted under 35 U.S.C. 154(b) by 458 days.

(21) Appl. No.: 12/918,238

(22) PCT Filed: Feb. 19, 2009

(86) PCT No.: PCT/US2009/001030
§ 371 (c)(1),
(2), (4) Date: Dec. 14, 2010

(87) PCT Pub. No.: WO2009/105210
PCT Pub. Date: Aug. 27, 2009

(65) Prior Publication Data
US 2011/0264027 A1  Oct. 27, 2011

Related U.S. Application Data

(60) Provisional application No. 61/066,374, filed on Feb. 19, 2008.

(51) Int. Cl.
*A61B 5/055* (2006.01)
*C07B 47/00* (2006.01)
*C07D 487/22* (2006.01)

(52) U.S. Cl.
USPC ......... 424/9.362; 424/9.61; 424/9.6; 540/145

(58) Field of Classification Search
None
See application file for complete search history.

(56) References Cited

U.S. PATENT DOCUMENTS 5,498,710 A * 3/1996 Pandey et al. .................. 540/145
5,591,847 A * 1/1997 Pandey et al. .................. 540/472
(Continued)

OTHER PUBLICATIONS

Liu et al., Highly Selective Synthesis of the Ring-B Reduced Chlorins by Ferric Chloride-Mediated Oxidation of Bacteriochlorins: Effects of the Fused Imide vs. Isocyclic Ring on Photophysical and Electrochemical Properties, J. Am. Chem. Soc., 2008, 130 (43), pp. 14311-14323, Publication Data (Web): Oct. 2, 2008, p. 14313; p. 14321.

(Continued)

*Primary Examiner* — Bong-Sook Baek
(74) *Attorney, Agent, or Firm* — Michael L. Dunn

(57) ABSTRACT

Tetrapyrrolic photosensitizers and imaging agent compounds having A, B, C, and D rings and having a reduced B ring and an oxidized D ring. The compounds preferably have a purity of at least 95 percent and preferably have a fused system connected at an unsaturated carbon atom of the C ring nearest the D ring and at the unsaturated carbon atom between the C and D rings. The invention also includes a method of making the compounds at over 95 percent yield by starting with a B and D ring oxidized tetrapyrollic compound and dissolving it in a halogenated hydrocarbon solvent and treating it with sufficient nitroalkane solution of $FeCl_3 6H_2O$ to oxidize the D ring and separating the resulting organic layer and drying.

8 Claims, 13 Drawing Sheets

(56) References Cited

U.S. PATENT DOCUMENTS

| | | |
|---|---|---|
| 5,770,730 A | 6/1998 | Pandey et al. |
| 2003/0165426 A1* | 9/2003 | Miura et al. ............... 424/1.65 |
| 2006/0198783 A1 | 9/2006 | Pandey et al. |

OTHER PUBLICATIONS

Chen, Y et al., Bioconjugate Chemi. 2007, 18, 1460-1473.

Jiao, Synthesis and Functionalizations of Tetrapyrrole Derivatives, Doctoral Dissertation, Louisiana State University and Agricultural and Mechanical College, pp. 1-211, Dec. 2007, p. 185, retrieved from http://etd.lsu.edu/docs/available/ltd-10232007-121548/unrestricted/Jiao_dis.pdf on Jul. 3, 2009.

* cited by examiner

Scheme 1.

10
Methyl bacteriopheophorbide-a

11
Methyl bacteriopyropheophorbide-a

Scheme 2:

Scheme 4:

Scheme 5:

Scheme 6:

Scheme 7:

B RING REDUCED-D RING OXIDIZED TETRAPYRROLIC PHOTOSENSITIZERS FOR PHOTODYNAMIC THERAPY AND TUMOR IMAGING

CROSS REFERENCE TO RELATED APPLICATIONS

This application claims priority from U.S. Provisional Application Ser. No. 61/066,374, filed Feb. 19, 2008 and is the National Stage of International Application No. PCT/US2009/001030, filed Feb. 19, 2009.

STATEMENT REGARDING FEDERALLY SPONSORED RESEARCH

This invention was made with government support under Grant Numbers CA114053 and CA119358 awarded by the National Institute of Health. The government has certain rights in this invention.

BACKGROUND OF THE INVENTION

Porphyrins (a tetrapyrrolic system) have generated enormous interest as photosensitizers for the use in photodynamic therapy. Photofrin®, a hematoporphyrin derivative developed at Roswell Park Cancer Institute (RPCI) is currently being used all over the world for treating a variety of cancers. Some of the disadvantages of Photofrin are (i) prolonged skin phototoxicity and the patients are advised to stay away from direct sunlight at least for 4 to 6 weeks after the treatment, (ii) weak absorption at 630 nm limits its tissue penetration ability, therefore the deeply seated tumors are difficult to cure. Efforts are underway in various laboratories, including ours to develop more tumor avid compounds than Photofrin with reduced skin phototoxicity.

The utility has recently been shown of porphyrin-based compounds and "Bifunctional Agents" for nuclear imaging (PET/SPECT) and therapy or to determine the ability of tumor-avid photosensitizer as vehicles to deliver the desired imaging agent (e.g. fluorescence imaging, MRI) to tumor for "see and treat approach. The applicability of this approach in fluorescence imaging/PDT by using 3-(1-hexyloxyethyl)-3-devinyl-pyropheophorbide-a (HPPH, currently in Phase II human clinical trials) as a tumor-targeting moiety has recently been shown.

PDT is increasingly acceptable as a curative or palliative treatment of cancer and some non-cancerous conditions that are generally characterized by overgrowth of transformed cells. Interest in this procedure was promoted by the recent approval of PDT with Photofrin® (a complex mixture of hematoporphyrin derivatives) by regulatory health authorities in several countries for the treatment of lung, gastric, esophageal, bladder and cervical tumors, in addition to cervical dysplasia and actinic keratosis. A more detailed understanding of the mechanisms involved in the photosensitized damage of cells and tissues, and better definition of correlations between chemical structure and photodynamic activity for various classes of porphyrin compounds, led to the development of second-generation photosensitizers with improved phototherapeutic properties. Some of these photosensitizers have proved useful for non-oncological indications such as the wet form of age-related macular degeneration (AMD).[1]

The successful outcome of PDT depends on the optimal interaction among three elements: light, photosensitizer and oxygen. In general, light in the red to near infrared region of the visible spectrum is outside the absorption bands of most endogenous absorbing molecules in human tissues. Consequently, the most frequently used PDT agents are porphyrins and their analogs (such as chlorins, bacteriochlorins and phthalocyanines) with absorption bands in the range of 630-800 nm. Recently, the availability of low-cost and compact red-emitting diode lasers that can be efficiently coupled with optical fibers, (allowing the irradiation of lesions in internal organs), has broadened the use of PDT.[1]

Although the mechanism of porphyrin retention by tumors is not well understood, the balance between lipophilicity and hydrophilicity is recognized as an important factor. In our laboratory, on the basis of SAR and QSAR studies, we have been able to determine the important structural parameters in photosensitizers related to pyropheophorbide-a (660 nm),[2] purpurinimides (700 nm)[3] and bacteriopurpurinimides (800 nm)[4]. These compounds are currently at various stages of clinical and pre-clinical trials. In our previous work developing 'dual-function' agents for tumor imaging and PDT, we have shown that tumor-avid photosensitizers can be used as targeting vehicles to deliver imaging agents to tumors. This approach has been quite successful in preparing optical imaging/PDT[5], PET imaging/PDT[6] and MR imaging/PDT agents[7]. However, efforts are underway to improve the tumor-selectivity of these 'bifunctional agents'.

In SAR studies with a series of alkyl- or aryl ether analogs of certain chlorins (ring D reduced) analogs, it has been observed that the (i) overall lipophilicity of the molecule and (ii) the presence of the substituent(s) at the variable peripheral position(s) of the molecule make a remarkable difference in tumor-uptake and PDT efficacy.

Previously in pyropheophorbide-a series (a chlorin system in which ring D is reduced), we synthesized and evaluated a series of alkyl ether analogs (e.g. compound 3 in Scheme 1, FIG. 7) for photosensitizing efficacy. We observed a parabolic relationship between the log P values (determines the overall lipophilicity of a compound) and the PDT activity and among these analogs the hexyl ether derivative (3a, HPPH) was found to be most effective. HPPH is currently under Phase II human clinical trials (Lung, Barrett esophagus and Head and neck cancer).

Recently, "Bifunctional Agents" for tumor imaging and PDT have been developed. Among a series of photosensitizers the iodobenzylether analog 5 exhibited excellent tumor imaging (PET imaging) and PDT efficacy.[5] The initial results obtained from the preliminary in vivo screening also suggest the utility of this compound in imaging tumor metastasis. The initial results obtained from the comparative study with F-18 fluorodeozyglucose (F-18 FDG) showed the superiority of compound 5 over F-18 FDG. However a detailed study with higher species is currently in progress.

So far, most of the chlorins derived from chlorophyll-a analogs in our and other laboratories contain ring-D reduced system. In our previous inventions, we have shown that presence of positions of certain substituents at various peripheral positions in chlorins (ring-D reduced) makes a significant effect in PDT efficacy.

BRIEF DESCRIPTION OF THE DRAWINGS

FIG. 7 shows scheme 1 of photosensitizers derived from pyropheophorbide-a for photodynamic therapy with and without PET imaging capability where A is PET and PDT agent with similar phamacodynamic and pharmacokinetic properties. *Spirulina Pacifica* contains mainly chlorophyll a.

BRIEF DESCRIPTION OF THE INVENTION

Figure 1:
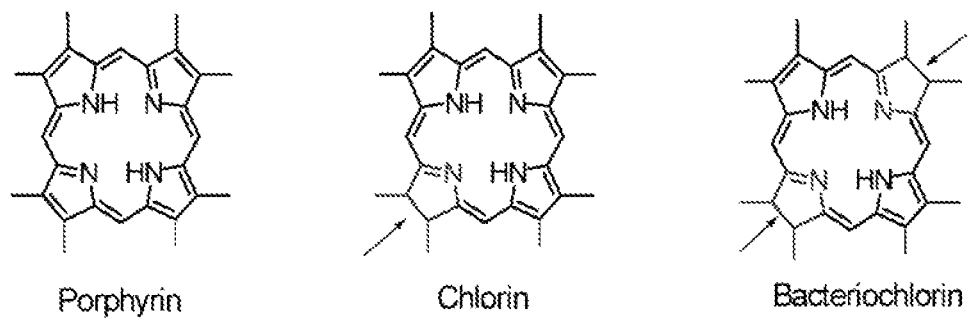
FIG. 1 shows basic structures of porphyrin, chlorin and bacteriochlorin.
Figure 2:
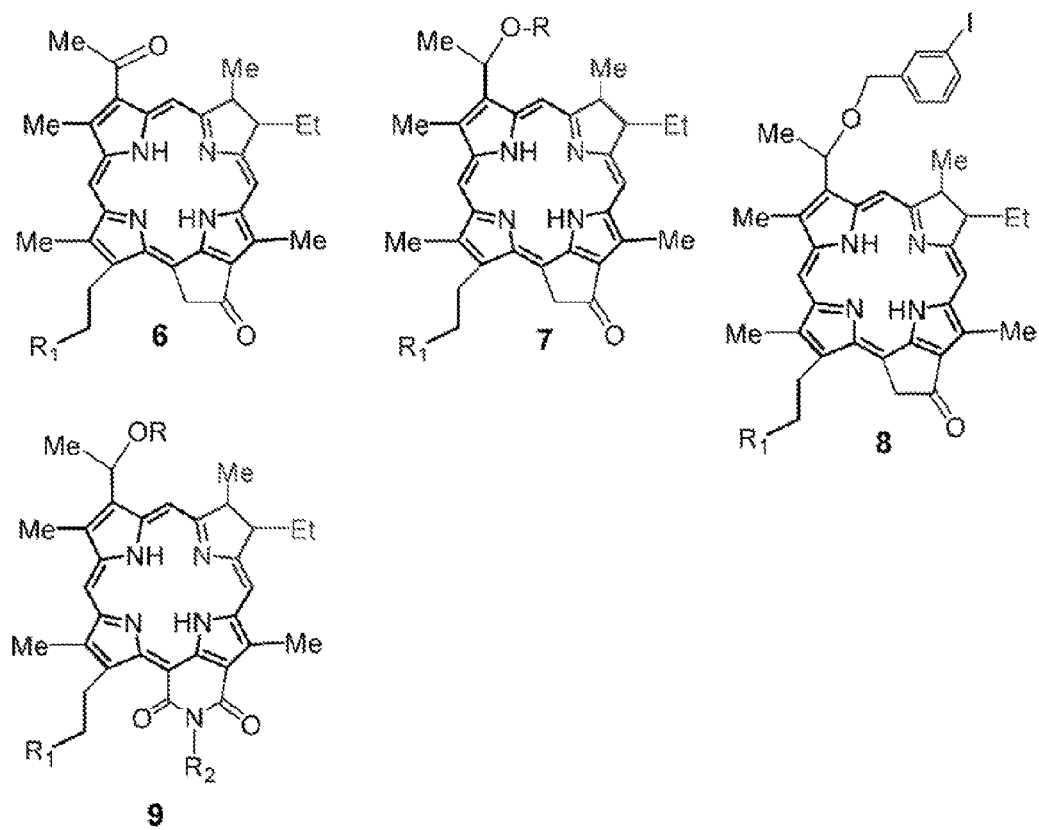
FIG. 2 shows structures of basic skeletons of chlorins derived from bacteriochlorophyll-a for PDT and tumor imaging in accordance with the invention. R=alkyl, aryl, PEG with variable length carbon chain and $R_1$=—COOH, esters, amides, amino acids, folic acid, monoclonal antibody, etc. moieties.

The present invention concerns a successful approach for the preparation of ring B reduced photosensitizers. The invention thus includes novel tetrapyrollic photosensitizers and imaging agents having a reduced B ring and an oxidized D ring. See e.g. 6-9 (FIG. 2). The photophysical properties, tumor uptake and PDT efficacy with the corresponding D ring reduced photosensitizers previously developed in our laboratory are compared.

Figure 8:
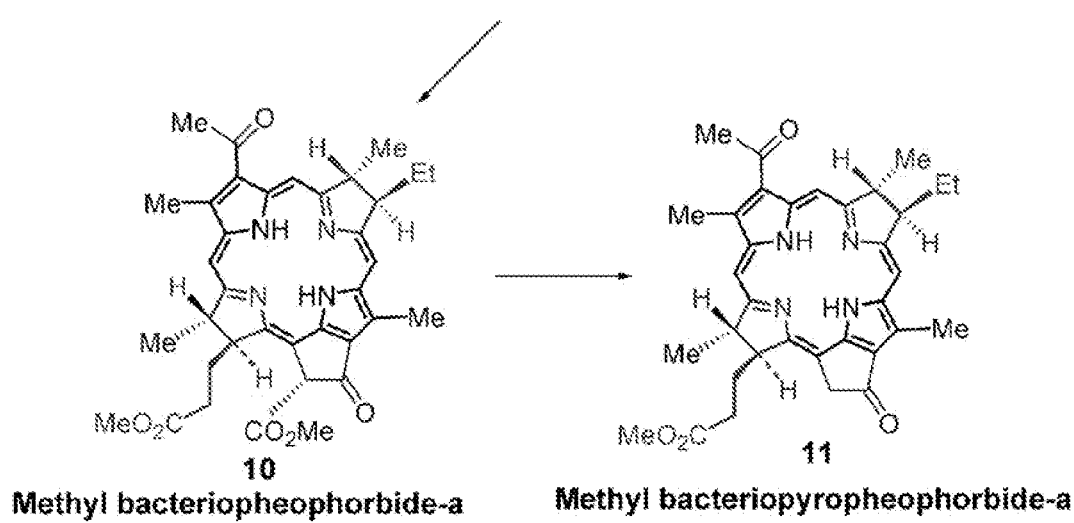
FIG. 8 shows scheme 2 for preparation of methyl bacteriopyropheophorbide-a. *Rb. shpaeroides* contains mainly bacteriochlorophyll-a.

To achieve the objective, methyl bacteriopheophorbide-a 10 was isolated from *Rb. sphaeroides* by following known methodology, i.e. Chen, Y et al., Bioconjugate Chemi. 2007, 18, 1460-1473, which on refluxing with collidine afforded methyl bacteriopyropheophorbide-a 11 (Scheme 2, FIG. 8) in excellent yield.

In accordance with the invention a purified tetrapyrollic compound having an oxidized D ring and reduced B ring is provided having photosensitizing or tumor imaging properties which compound has the following structural formula:

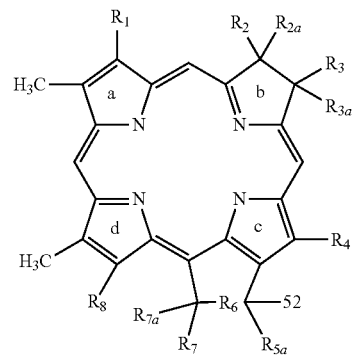

where:

$R_1$ is —CH=CH$_2$, —CH$_2$CH$_3$, —CR$_{13}$O where $R_{13}$ is hydrogen, lower alkyl or substituted lower alkyl, —COOH, or

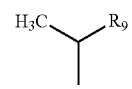

where $R_9$=—OR$_{10}$ where $R_{10}$ is —H, lower alkyl of 1 through 8 carbon atoms, aryl, polyalkylene glycol group of up to 20 carbon atoms, —CH$_2$R$_{14}$ where $R_{14}$ is phenyl or substituted phenyl, —(CH$_2$—O)$_n$CH$_3$, —(CH$_2$)$_2$CO$_2$CH$_3$, —(CH$_2$)$_2$CONHphenyleneCH$_2$DTPA, —CH$_2$CH$_2$CONH (CONHphenyleneCH$_2$DTPA)$_2$, —CH$_2$R$_1$ or

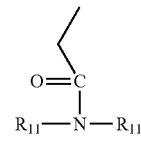

or a fluorescent dye moiety; $R_2$, $R_{2a}$, $R_3$, $R_{3a}$, $R_4$, $R_5$, $R_{5a}$, $R_7$, $R_{7a}$, and $R_{13}$ are independently hydrogen, lower alkyl or substituted lower alkyl or two, $R_5$, $R_{5a}$, $R_7$, and $R_{7a}$ groups on adjacent carbon atoms may be taken together to form a covalent bond or two $R_2$, $R_{2a}$, $R_3$, $R_{3a}$, $R_5$, $R_{5a}$, $R_7$, and $R_{7a}$ groups on the same carbon atom may form a double bond to a divalent pendant group; $R_2$ and $R_3$ may together form a 5 or 6 membered heterocyclic ring containing oxygen, nitrogen or sulfur; $R_6$ is —CH$_2$—, —C(O)O(O)C—, —N(R$_{12}$)— or a covalent bond; $R_8$ is —(CH$_2$)$_2$COR$_{15}$ where $R_{15}$ is —OH, —O-lower alkyl of up to 8 carbon atoms, aryl, —NH$_2$, amino acid residue, or an antibody residue; —(CH$_2$)$_2$CONHphenyleneCH$_2$DTPA, —CH$_2$CH$_2$CONH(CONHphenyleneCH$_2$DTPA)$_2$, —CH$_2$R$_{11}$ or

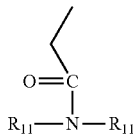

where R$_{11}$ is —CH$_2$CONH-RGD-Phe-Lys, —CH$_2$NHCO-RGD-Phe-Lys, a fluorescent dye moiety, or —CH$_2$CONHCH$_2$CH$_2$SO$_2$NHCH(CO$_2$)CH$_2$NHCO-phenylOCH$_2$CH$_2$NHcycloCNH(CH$_2$)$_3$N; where R$_{12}$ is hydrogen, lower alkyl or substituted lower alkyl; and polynuclide, radioisotope and X complexes thereof where X is a metal selected from the group consisting of Zn, In, Ga, Al, Mn, Pd or Cu or a radioisotope labeled moiety wherein the radioisotope is selected from the group consisting of $^{11}$C, $^{18}$F, $^{64}$Cu, $^{124}$I, $^{124}$I, $^{131}$I, $^{99}$Tc, $^{111}$In, and GdIII The complexes with X are readily made simply by heating the compound with a salt of X such as a chloride.

The invention also includes a unique method of making the above compounds at over 95 percent yield by starting with a B and D ring oxidized tetrapyrollic compound and dissolving it in a halogenated hydrocarbon solvent and treating it with sufficient nitroalkane solution of FeCl$_3$.6H$_2$O to oxidize the D ring and separating the resulting organic layer and drying. The method of the invention may be used to treat a B and D ring reduced chlorin to obtain a B ring reduced -D ring oxidized chlorin. This, for example may be used to convert B and D ring reduced tetrapyrollic compound having a fused anhydride or fused N-substituted imide ring system, at the unsaturated carbon atom of the C ring nearest the D ring and at the unsaturated carbon atom between the C and D rings, to obtain the corresponding B ring reduced -D ring oxidized compound.

The compound will form as a chelate of a -DTPA moiety, when present, or within the tetrapyrollic structure between the nitrogen atoms of the amine structure or both. Examples of such structures are:

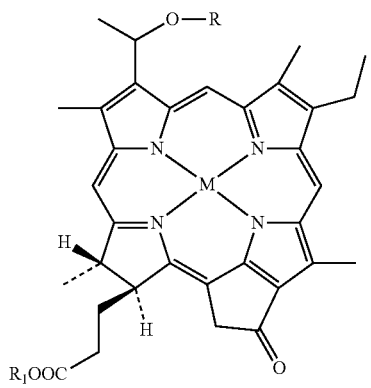

M=2H or
M=In, Cu, Ga (with or without radioactive isotope)

and

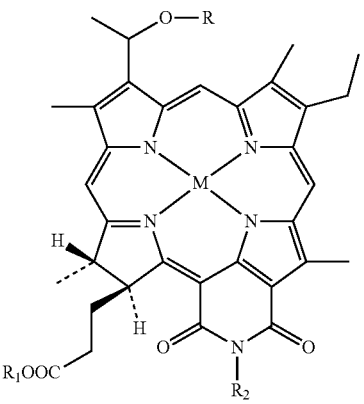

M=2H or
M=In, Cu, Ga (with or without radioactive isotope)
Where X=M

DETAILED DESCRIPTION OF THE INVENTION

Figure 9:
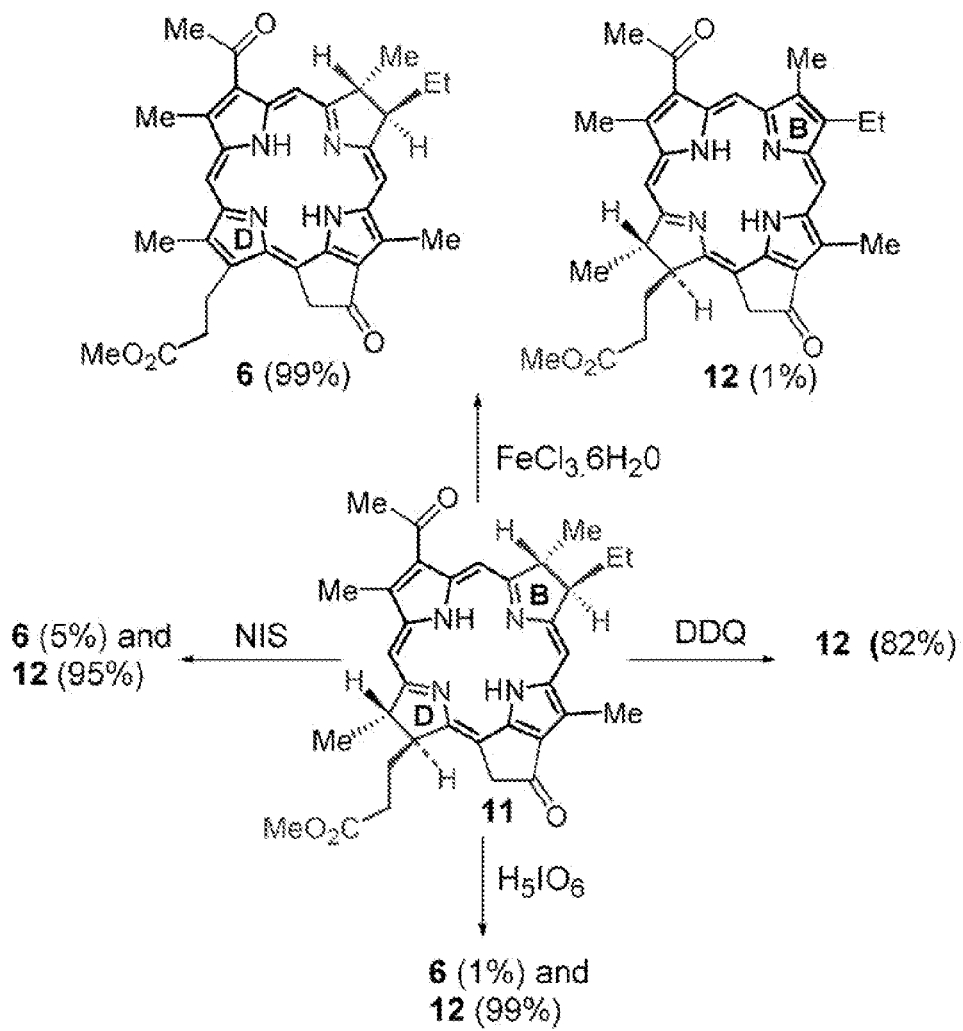
FIG. 9 shows scheme 3 for oxidation of bacteriopyropheophorbide 2 with various oxidizing agents where the use of DDQ results in decomposition products in addition to 82% yield.

The utility of various oxidizing agents for regioselective oxidation (ring D over ring B) of bacteriochlorin 11 was investigated. As shown in Scheme 3, FIG. 9, most of the oxidizing agents (DDQ, NIS, H$_5$IO$_6$) on reacting with compound II afforded mainly the ring B oxidized chlorin 12 (methyl 3-acetyl-3-devinylpyropheophorbide-a) in more than 95% yield. However, to our surprise the ferric chloride (FeCl$_3$) oxidation exclusively produced ring D oxidized chlorin 6. Interestingly, it happens to be a first example to show the remarkable utility of FeCl$_3$ in regioselective oxidation of ring D in bacteriochlorin system. In this invention, we demonstrate a new approach for an easy access for the synthesis on novel chlorin system (B ring reduced and D ring oxidized) from readily available bacteriochlorophyll-a (Scheme 3, FIG. 9).

Figure 10:
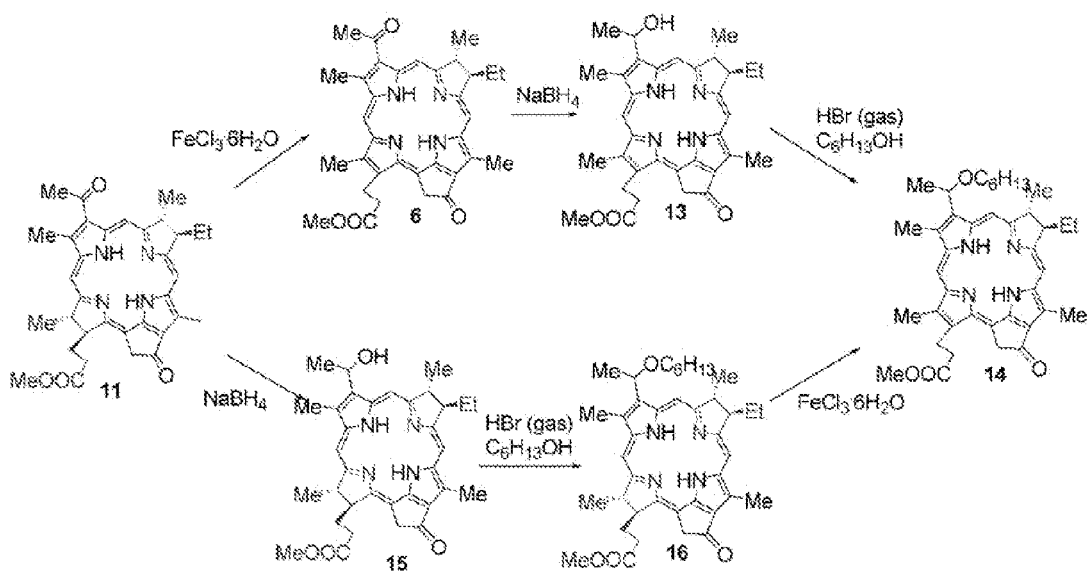
FIG. 10 shows scheme 4 for synthetic strategies for the preparation of B-ring reduced chlorins.

After having the desired new chlorin 6 (ring B reduced) in hands, our goal was to develop efficient synthetic methodologies for the preparation of its 3-(1'-hexyloxyethyl) derivative 14 (Scheme 4, FIG. 10) and to compare its efficacy with HPPH (a structural isomer in which ring D is reduced). The two synthetic strategies used for the preparation of 14 is shown in Scheme 4. Both approaches gave the desired analog. However, the oxidation of 12 with FeCl$_3$ to produced 13, which on subsequent reactions with sodium borohydride (NaBH$_4$) and HBr/hexanol afforded the desired hexyl ether derivative 14 in a better overall yield and therefore proved to be a better synthetic approach.

Figure 11:
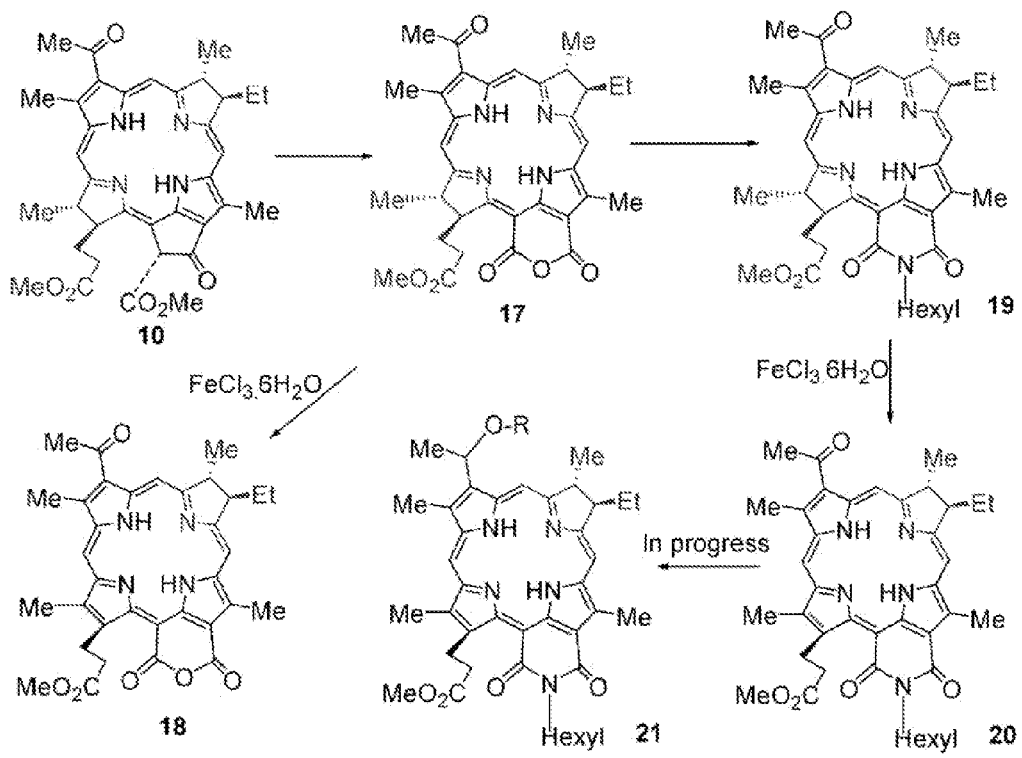
FIG. 11 shows scheme 5 of a first synthesis of ring-B reduced chlorins containing a fused anhydride or N-substituted imide ring system where R=alkyl, aryl or PEG substituent.

We further explored the utility of ferric chloride oxidation in other bactiochlorin systems containing a fused six member anhydride 17 or N-substituted imide ring system 19. Similar to the results obtained from the bacteriochlorins containing a fused 5-member isocyclic ring, these compounds also produced exclusively B-ring reduced (D ring oxidized) chlorins 18 and 20 respectively in 100% yields (Scheme 5, FIG. 11).

Highly Effective Metallated Photosensitizers: Porphyrins are one of the best ligands for preparing metal complexes in terms of thermodynamic stability. Many of the naturally occurring porphyrins (heme, chlorophylls a and b, vitamin B12) are metal bounded and do not show any toxicity on living organisms. It is well known that the nature of the metal present in the porphyrin ring alters its photochemical and photophysical properties. The central metal and its electronic properties are also responsible for the photocytotoxic potential of the porphyrins. Certain diamagnetic metals increase the life time of triplet excited state of the photosensitizer, which increases its triplet quantum yield. Since, the triplet quantum yield is directly related to the efficiency of generating singlet oxygen, the metal which generates longer life time of the triplet state should be more effective singlet oxygen producing agent. Recently, considerable number of metallated PS related to chlorins, bacteriochlorins and phthalocyanines are at various stages of clinical trials. Among the metallated analogs, the Pd(II) complex of bacteriopheophorbide a (WST09 or Tookad) is of particular interest. It is highly singlet oxygen generating agent (100%) without any fluorescence producing efficiency. Unfortunately, due to its poor pharmacokinetics it does not retain in tumors for a long time and due to a very short "treatment window" drug infusion and light delivery must be simultaneously performed, which under clinical conditions is not very practical. In a series of the Gallium complexes of alkyl ether analogs of hematoporphyrin-aspartic acid derivatives Nakae and coworkers[9] have shown that the presence of Gallium and the overall lipophilicity of the molecule play important role in tumor uptake and PDT efficacy. Among the compounds tested, the Gallium complex of HP-Asp bearing two 10-carbon units showed the maximum efficacy. However, for improving the PDT efficacy, complexing hematoporphyrin analogs with gallium is not an ideal approach because PS-wavelength absorption falls below 630 nm.

Figure 12:
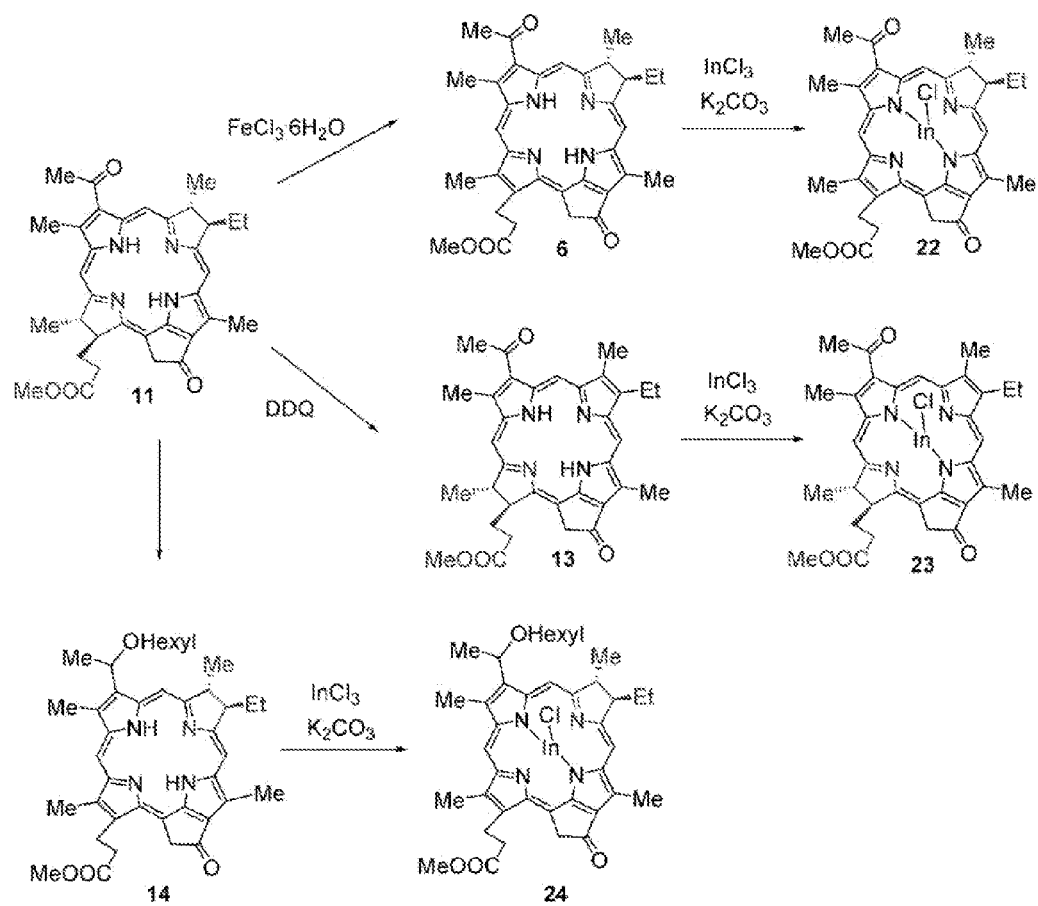
FIG. 12 shows scheme 6 for synthesis of In (III) complexes of chlorins of the invention.

We have previously shown that compared to nonmetallated analogs, the corresponding Indium complexes of HPPH (ring-B reduced chlorine) show enhanced PDT efficacy. These metallated analogs also produce higher singlet oxygen production, higher stability and a significantly reduced rate of photobleaching under variable light dosimetry. Therefore, our interest was to investigate the effect of certain metal complexes (e.g. In, Pd and Ga) of highly tumor-avid new B-ring reduced chlorins. In our initial study chlorins 13, 14 and 16 were converted to the corresponding In(III) complexes 22-24 respectively (Scheme 6, FIG. 12). In preliminary screening, these compounds were found to be highly effective (see the biological studies part of this invention). The in vivo biological investigation of the free-base and the metallated analogs are currently in progress.

Figure 7:
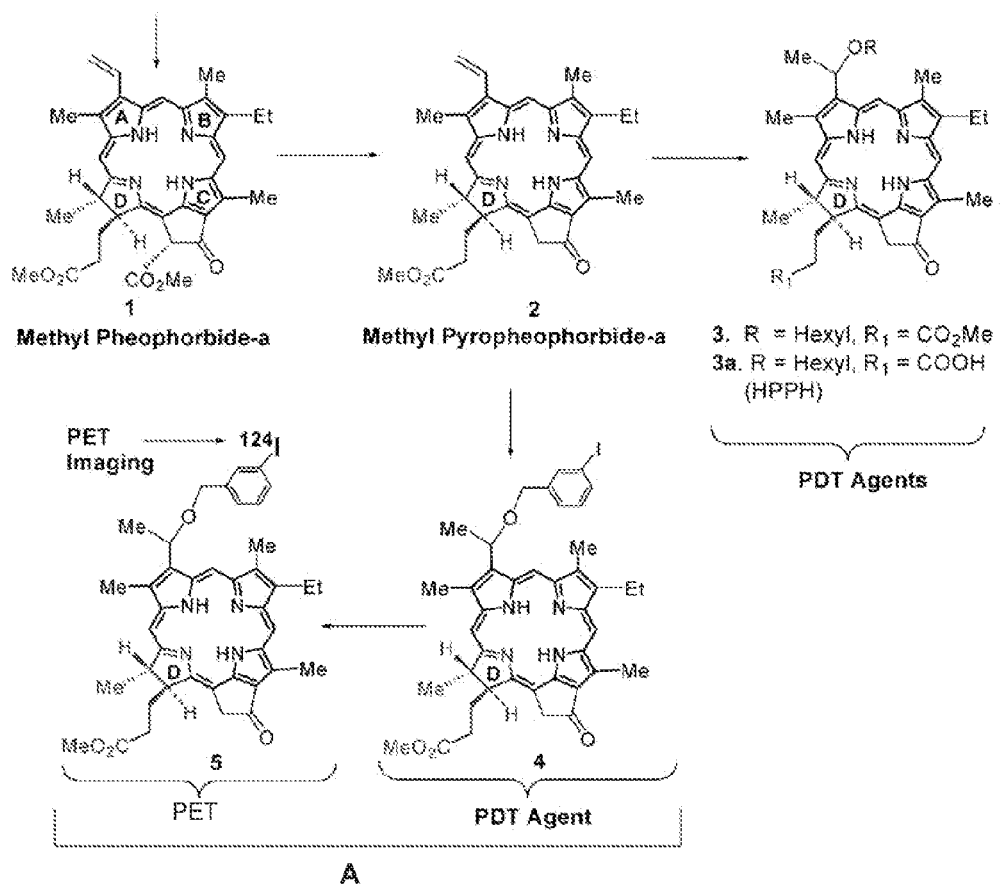
Figure 13:
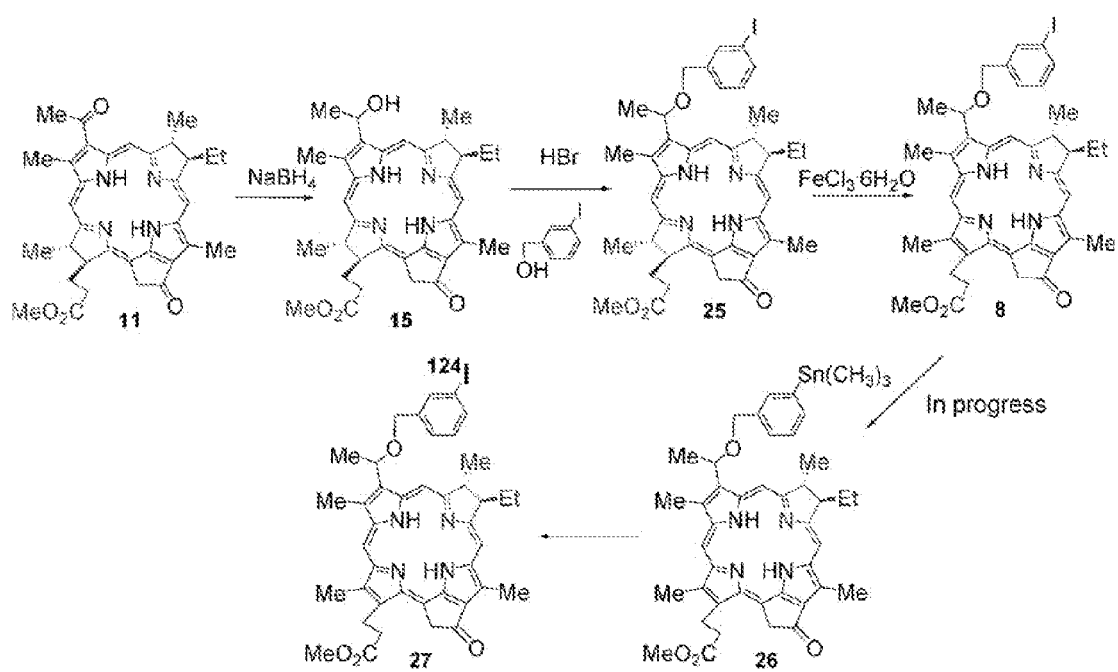
FIG. 13 shows scheme 7 for synthesis of B-ring reduced chlorin containing an iodobenzyl ether substituent and the corresponding I-124 labeled analog for PET imaging and PDT.

Improved Bifunctional Agents for PET Imaging and PDT: In pyropheophorbide-a system we have previously shown that introduction of iodobenzyl ether substituent at position-3 of the molecules and replacement of cold iodine with I-124 make it a suitable candidate for imaging (PET) and photodynamic therapy (Scheme 1, FIG. 7). The long half life of I-124 (4.2 days) compliments with the optimal tumor uptake (24 to 48 h) and pharmacokinetics of the photosensitizer. Therefore, our interest was to introduce the same substituent in our new chlorin system 8 (FIG. 2) and compare the tumor uptake and photosensitizing efficacy with the related pyropheophorbide-a analog 4 and PET imaging with I-124 analog 5 (Scheme 1, FIG. 7). The synthetic approach for the preparation of the desired iodinated photosensitizer 8 and the corresponding I-124 analog 27 from the bacteriochlorin 11 is shown in Scheme 7, FIG. 13.

Figure 3:
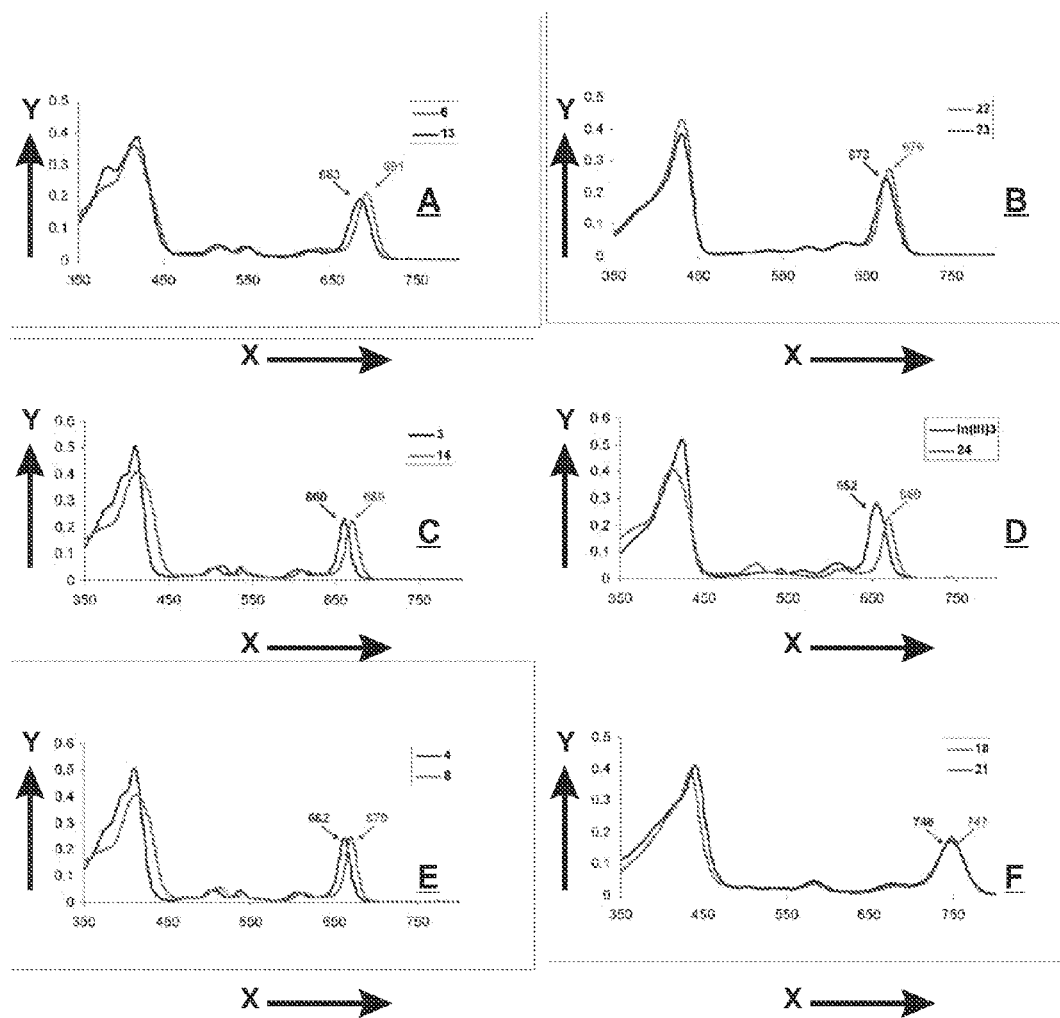
FIG. 3, in graphs A-F, shows curves of comparative electronic absoption spectra of photosensitizers of various B-ring and D-ring reduced chlorins derived from chlorophyll-a and bacteriochlorophyll-a at equimolar concentrations at 5 µM in dichloromethane, where legend compound numbers refer to compounds shown in FIGS. 7-12.
Figure 4:
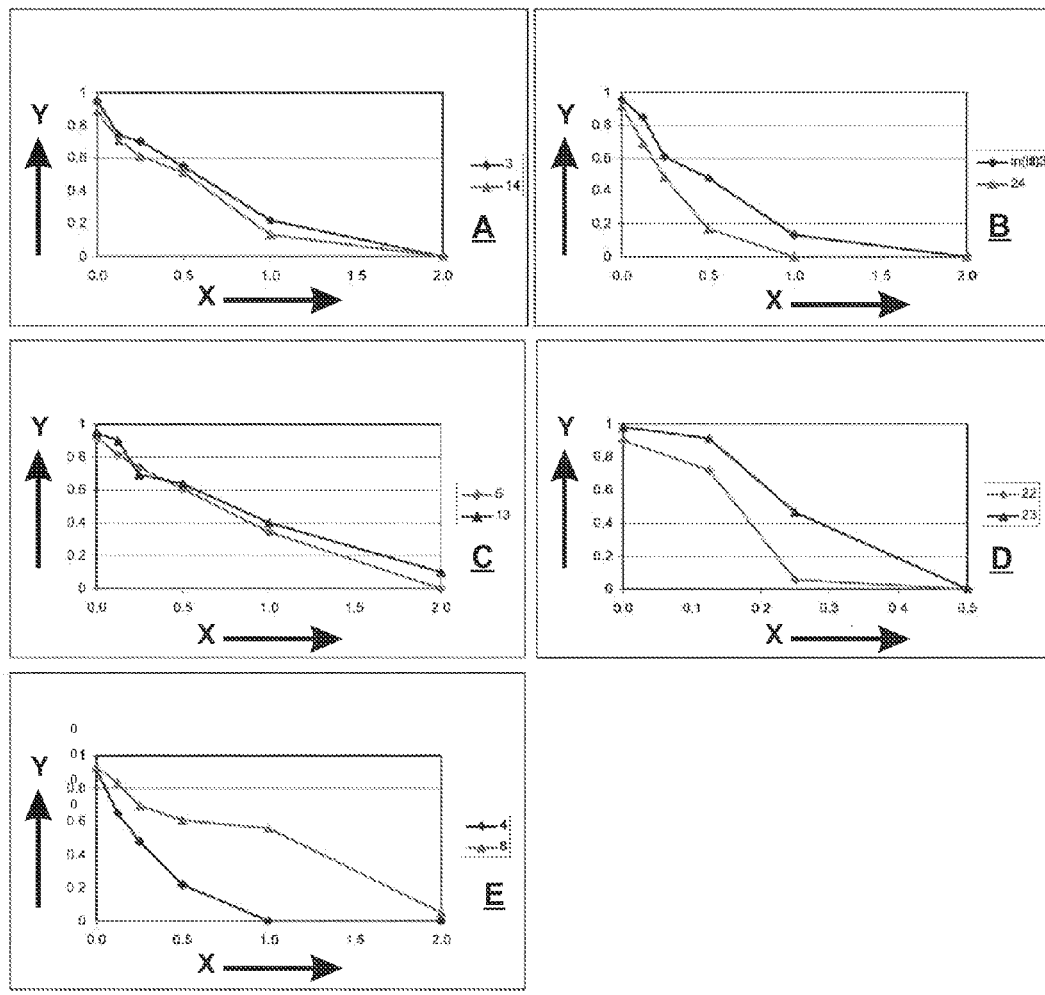
FIG. 4 shows comparative in vitro photosensitizing efficacy of various free-base and In(III) complexes of photosensitizers derived from chlorophyll-a and bacteriochlorophyll-a in colon-26 tumor cells. In graphs A-E, Y=fraction surviving and X=Light dose in J/cm$^2$. The numbers in the legends refer to compound number in FIGS. 7-12. A shows photosensitivity at a concentration of 0.125 µM. B-D show photosensitivity at a concentration of 0.031 µM. and E shows photosensitivity at a concentration of 0.25 µM.

Photophysical Properties: Some of the key requirements for an effective photosensitizer are to have long-wavelength absorption>650 nm with high extinction coefficient values, high singlet oxygen producing efficiency, high tumor avidity and less uptake in skin and the surrounding muscles. Therefore, we compared the electronic absorption spectra of our new photosensitizers (B ring reduced chlorin) derived from bacteriochlorophyll-a with D-ring reduced chlorins obtained from chlorophyll-a. As can be seen from the results summarized in FIG. 3, compared to ring-D reduced chlorins derived from chlorophyll-a, the ring-B reduced chlorins obtained from bacteriochlorophyll-a exhibited longer wavelength absorptions. Interestingly, the chlorins containing fused anhydride 18 and imide ring 21 systems showed strong long-wavelength absorptions>745 nm.

In vitro Photosensitizing Efficacy (MTT Assay]: Colon-26 cells were grown in α-DMEM with 10% fetal calf serum, and penicillin and streptomycin. Cells were maintained in 5% $CO_2$ and 95% air at 100% humidity. For phototoxicity studies, cells were placed in 96-well plates at a density of $5 \times 10^4$ cells/well, in complete medium. 24 h later, compounds were added at variable concentration. After 24 incubation in the dark at 37° C., the cells were irradiated with a laser light from an argon pumped dye laser using flunces of 0-2 $J/cm^2$ at a dose of 5.6 $mW/cm^2$. After PDT, the cells were washed once, placed in complete medium, and incubated for 48 h. Cells were incubated with 10 μL/well of 4 mg/mL MTT for the final 4 h. The MTT-containing medium was removed, and 100 μL DMSO was added to solubilize the formazan crystals. The absorbance of the wells was read on a microtiter plate reader at a wavelength of 560 nm.[10] The results were plotted as fraction survival vs. the light dose used at the same concentrations. As can be seen among all the compounds, compared to the free-base analogs the corresponding In(III) complexes produced enhanced activity. Interestingly, the effect of substitutions at the peripheral positions also showed a significant difference in activity. For example, among all the compounds tested so far, compounds containing the acetyl group at position-3 22 and 23 were most effective and in general (except 4 and 8) compared to D-ring reduced chlorins, the ring B-reduced chlorins were found to be more effective. These compounds are currently being evaluated for in vivo efficacy, where the pharmacokinetic and the pharmacodynamic properties of the molecules will have a significant impact in efficacy.

In vivo tumor uptake: The tumor vs. skin/muscle uptake of photosensitizers 3 and 14 was determined by in vivo reflectance spectroscopy. The in vivo reflection data were collected by delivering monochromatic light through a quartz fiber in contact with the tissue (tumor and skin) in question. At a measured distance (typically approximately 5 mm) from the delivery fiber, a pickup fiber was placed in contact with the surface. Both fibers were perpendicular to the tissue surface. Very low optical power levels (1 μW) was necessary in these experiments to avoid PDT effects during measurement. Light that entered the pickup fiber was conducted to a silicon photodiode detector. The detector circuit measured the photocurrent that was linear in power over 7-8 orders of magnitude. Because of the optical properties of the tissue, the spectral range of greatest utility in the region between 600 and 1000 nm. In this spectral range, the probability of diffuse scattering of photons by laser is greater than the probability of absorption. The wavelength of the light was varied by scanning the monochromator, and a spectrum of diffusely scattered photons was recorded. To calculate the concentration, we used the longest absorption wavelength by following the well established methodology.

Figure 5:
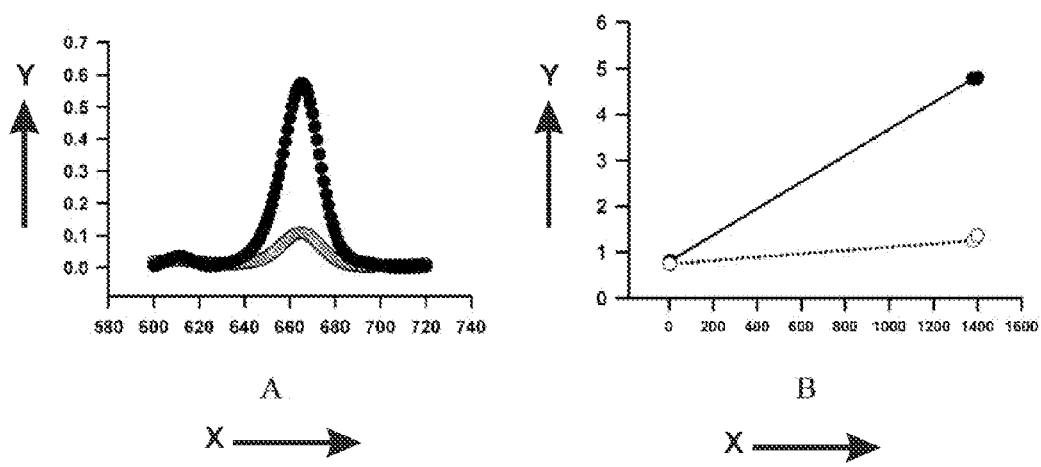
FIG. 5 at A shows in vivo reflectance spectra of compound 3a at 24 hours post injection (tumor solid line, skin hollow line) where Y=OD (base e) and X=wavelength in nm and B shows ratio of micromolar concentration of the photosensitizer in tumor to skin (ratio 4:1) at Y and X shows minutes post injection.
Figure 6:
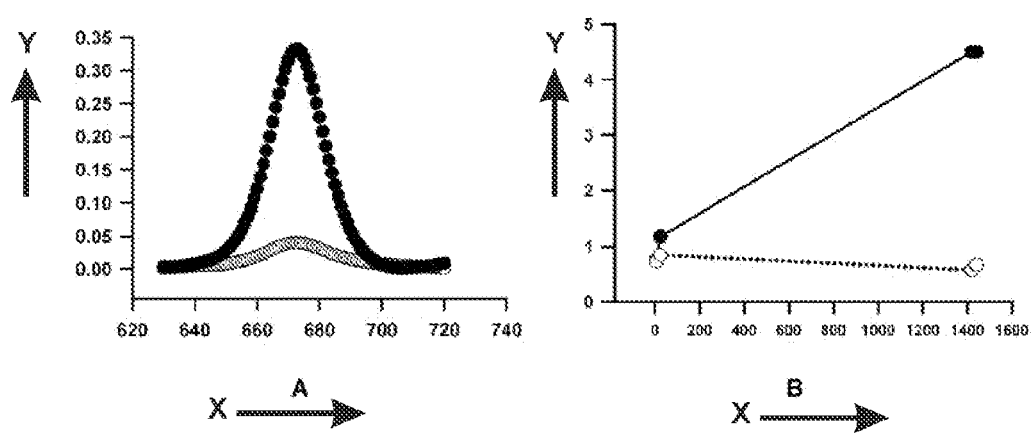
FIG. 6 at A shows In vivo reflectance spectra of compound 14 at 24 h post injection (tumor: solid line, skin: hollow line) where Y=OD (base e) and X=wavelength in nm and at B, X is minutes post injection and Y shows micromolar concentration of the photosensitizer in tumor vs. skin (ratio-9:1), which was significantly higher than that observed with HPPH-methyl ester (FIG. 5).

The tumor to skin uptake of HPPH methyl ester 3 and the related B-ring reduced chlorin 14 with similar lipophilicity (5.0 mmol/kg) were measured by in vivo reflectance spectroscopy. In a typical experiment, the photosensitizers were individually injected in BALB/c mice bearing Colon-26 tumors and the in vivo absorption was taken at variable time points. The tumor and skin absorption spectra and the concentrations of the photosensitizers in these sites at 24 h post-injection are shown in FIGS. 5 and 6 respectively. Under similar experimental conditions the tumor vs. skin uptake of ring B reduced chlorin was also measured. As can be seen from FIGS. 5 and 6 both photosensitizers showed high tumor uptake. However, the tumor to skin ratio with compound 14 was 9:1, and it was significantly higher ratio than that observed with compound 3a, which suggest that chlorin 14 should show reduced skin phototoxicity than 3a Advantages of the Invention (i) The starting material (Rb. sphaeroides) for the synthesis of new B-ring reduced chlorines is readily available.
(ii) The preparation of the desired compounds require limited synthetic steps with high yields.
(iii) Compared to HPPH 3a (ring D reduced chlorin), which is currently in Phase I/II human clinical trials, the chlorin 14 (ring B reduced) with similar lipophilicity produced higher tumor to muscle ratio, longer wavelength absorption and higher in vitro PDT efficacy.
(iv) Compared to the free base analogs 6, 14 the corresponding In(III) analogs 22 and 24 respectively produced enhanced PDT efficacy. The replacement of cold Indium with In-111 could provide PDT agent with SPECT imaging ability (dual-function agents).
(v) The new B-ring reduced iodobenzyl chlorin 8 also exhibited high tumor avidity. The related I-124 analog could be useful for PET imaging and PDT.
(vi) Starting from bacteriochlorophyll-a, we have developed a new and efficient synthesis for the preparation of novel chlorin systems (containing either a five member isocyclic ring or a six member fused anhydride ring or a six member fused N-substituted imide ring system). All these analogs show longer wavelength absorptions than the corresponding D-ring reduced chlorins.
(vii) Due to higher tumor avidity and long wavelength absorption, these compounds should be extremely useful for developing "multifunctional agents" for imaging (fluorescence, PET/SPECT) and photodynamic therapy of cancer.

Synthesis and Characterization of New Photosensitizers:

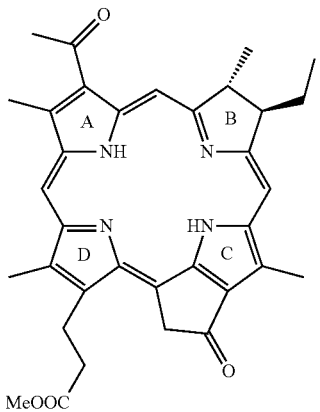

B ring reduced Chlorin 6: Bacteriopyropheophorbide-a 11 (50.0 mg, 0.0883 mmol, 1.0 equiv) was dissolved in dichloromethane (50 mL). To this mixture was added slowly a nitromethane (4 mL) solution of $FeCl_3 \cdot 6H_2O$ (95.5 mg, 4.0 equiv). The resulting reaction mixture was stirred at room temperature for 30 min and washed with $H_2O$ three times. Organic layer was separated, dried from $Na_2SO_4$, and evaporated to dryness. The solid obtained is pure enough for the next step. Yield: 49.0 mg, 99%. $^1H$ NMR (400 MHz, $CDCl_3$) δ: 9.41 (s, 1H, 10-H), 9.32 (s, 1H, 5-H), 8.72 (s, 1H, 20-H), 5.44 (s, 2H, $13^1$-$CH_2$), 4.53 (q, J=4.8 Hz, 1H, 7-H), 4.27 (br s, 1H, 8-H), 3.85 (t, J=6.8 Hz, 2H, 17-$CH_2$), 3.75 (s, 3H, $COOCH_3$), 3.70 (s, 3H, 12-$CH_3$), 3.58 (s, 3H, 2-$CH_3$), 3.24 (s, 6H, 18-$CH_3$+$CH_3CO$), 2.92 (t, J=7.2 Hz, 2H, $17^1$-$CH_2$), 2.47-2.48 (m, 1H, $8^1$-H), 2.15-2.22 (m, 1H, $8^1$-H), 1.92 (d, J=6.8 Hz, 3H, 7-$CH_3$), 0.89 (t, J=6.4 Hz, 3H, $8^1$-$CH_3$), −0.68 (br s, 1H, NH), −1.61 (br s, 1H, NH). MS (ESI) m/z: 565.3 ($M^+$+1). UV-vis, $CH_2Cl_2$, $\lambda_{max}$ nm (ε): 691 (4.31×$10^4$), 638 (8.32× $10^3$), 550 (9.78×$10^3$), 517 (1.04×$10^4$), 415 (7.39×$10^4$).

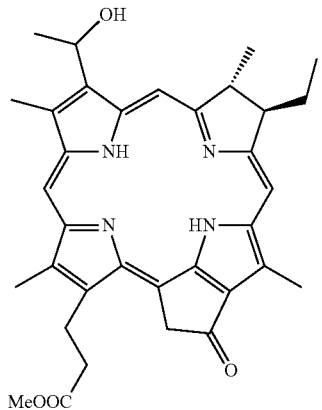 [SMILES: CC[C@H]1c2cc3[nH]c4c(c5nc(cc6[nH]c(cc(n2)[C@@H]1C)c(C(C)O)c6C)C(C)=C5CCC(=O)OC)CC(=O)c4c3C]

Chlorin 13: Compound 6 (40.0 mg, 0.0108 mmol, 1.0 equiv) was dissolved in dichloromethane/methanol (20 mL, 4:1 v/v). Sodium borohydride (10.8 mg, 4.0 equiv) was added to it. The mixture was stirred at room temperature for 6 hr and washed with $NaHCO_3$ saturated solution, brine, and water successively. Organic layer was separated, dried from $Na_2SO_4$, and evaporated to dryness. The residue was purified by flash column chromatography (silica gel, 5% acetone in $CH_2Cl_2$). Yield: 27.3 mg, 68%. $^1H$ NMR (400 MHz, $CDCl_3$) δ: 9.03 (s, 1H, 10-H), 9.01 (d, J=11.6 Hz, 5-H), 8.64 (s, 1H, 20-H), 6.38 (q, J=6.4 Hz, 1-H, $3^1$-H), 5.20 (s, 2H, $13^1$-$CH_2$), 4.47-4.50 (m, 1H, 8-H), 4.22-4.24 (m, 1H, 7-H), 3.74 (s, 3H, $COOCH_3$), 3.51-3.57 (m, 5H, 17-$CH_2$+12-$CH_3$), 3.46 (d, 3H, 8-$CH_3$), 3.03 (d, 3H, 18-$CH_3$), 2.77-2.81 (m, 2H, $17^1$-$CH_2$), 2.45-2.52 (m, 1H, $8^1$-H), 2.16 (d, J=6.4 Hz, 4H, $8^1$-H+$3^1$-$CH_3$), 1.91-1.94 (m, 3H, 7-$CH_3$), 1.17-1.20 (m, 3H, $8^1$-$CH_3$), −0.55 (br s, 1H, NH), −1.66 (br s, 1H, NH). MS (ESI) m/z: 567.5 ($M^+$+1). UV-vis, $CH_2Cl_2$, $\lambda_{max}$ nm (ε): 669 (3.41×$10^4$), 611 (5.57×$10^3$), 539 (5.39×$10^3$), 512 (9.01×$10^3$), 410 (7.03× $10^4$).

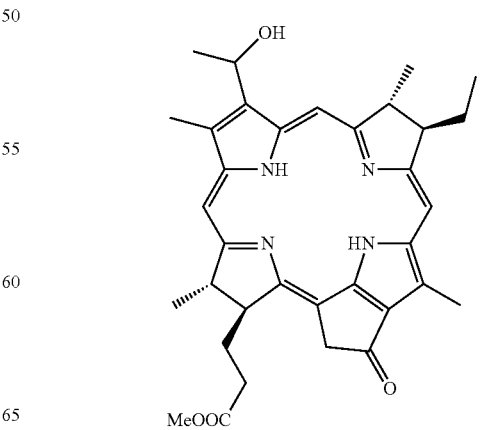

Bacteriochlorin 15: Bacteriopyropheophorbide-a 10 (50.0 mg, 0.0883 mmol, 1.0 equiv) was dissolved in dichloromethane/methanol (25 mL, 4:1 v/v). Sodium borohydride (33.6 mg, 10 equiv) was added to it. The mixture was stirred at room temperature for 4 hr and washed with $NaHCO_3$ saturated solution, brine, and water successively. Organic layer was separated, dried from $Na_2SO_4$, and evaporated to dryness. The solid obtained is pure enough for the next step. This compound was reported by Tamiaki et al. [Tamiaki, H.; Kouraba, M.; Takeda, K.; Kondo, S.-i.; Tanikaga, R. *Tetrahedron Asymmetry* 1998, 9, 2101-2111]. Yield: 49.7 mg, 99%. $^1$H NMR (400 MHz, $CDCl_3$) δ: 8.51 (s, 1H, 10-H), 8.22 (s, 1H, 10-H), 8.02 (s, 1H, 20-H), 6.18 (q, J=5.6 Hz, 1H, $3^1$-H), 4.96 (d, J=20 Hz, 1H, $13^2$-H), 4.78 (d, J=20 Hz, 1H, $13^1$-H), 4.12-4.16 (m, 2H, 7-H+18-H), 3.98-4.00 (m, 1H, 17-H), 3.88-3.90 (m, 1H, 8-H), 3.62 (s, 3H, $COOCH_3$), 3.35 (s, 3H, 12-$CH_3$), 3.21 (s, 3H, 2-$CH_3$), 2.17-2.57 (m, 6H, $8^1$-$CH_2$+17-$CH_2$+$17^1$-$CH_2$), 2.04 (d, J=6.4 Hz, 3H, $3^1$-$CH_3$), 1.66-1.77 (m, 6H, 7-$CH_3$+18-$CH_3$), 1.12 (t, J=7.2 Hz, 3H, $8^1$-$CH_3$), −0.22 (s, 1H, NH).

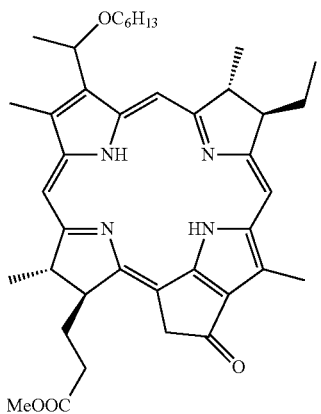

Bacteriochlorin 16: Following the procedure described for the synthesis of 14, treatment of 15 (50.0 mg, 0.0879 mmol, 1.0 equiv) with HBr gas, $C_6H_{13}OH$ (0.1 mL), and $K_2CO_3$ (50 mg) resulted in the desired product. Purification was done by flash column chromatography (silica gel, 50% ethyl acetate in hexane). Yield: 43.0 mg, 75%. $^1$H NMR (400 MHz, $CDCl_3$) δ: 8.53 (t, 1H, 5-H), 8.20 (s, 1H, 10-H), 7.99 (s, 1H, 20-H), 5.60-5.66 (m, 1H, $3^1$-H), 4.96 (d, J=20.0 Hz, 1H, $13^1$-H), 4.78 (d, J=20.0 Hz, 1H, $13^1$-H), 4.09-4.15 (m, 2H, 7-H+8-H), 3.99 (d, 1H, 17-H), 3.87-3.89 (m, 1H, 8-H), 3.62 (s, 3H, $COOCH_3$), 3.51-3.59 (m, 2H, $3^1$-$OCH_2$), 3.35 (s, 3H, 12-$CH_3$), 3.15 (s, 3H, 2-$CH_3$), 2.44-2.57 (m, 2H, $8^1$-H+$17^1$-H), 2.19-2.33 (m, 3H, $17^1$-H+$17^1$-$CH_2$), 1.99-2.02 (m, 1H, $8^1$-H), 1.98 (d, J=6.4 Hz, 3H, $3^1$-$CH_3$), 1.67-1.78 (m, 8H, 7-$CH_3$+18-$CH_3$+$3^1$-$OCH_2CH_2CH_2CH_2CH_2CH_3$), 1.24-1.36 (m, 6H, $3^1$-$OCH_2CH_2CH_2CH_2CH_2CH_3$), 1.10-1.15 (m, 3H, $3^1$-$OCH_2CH_2CH_2CH_2CH_2CH_3$), 0.82 (t, J=6.0 Hz, 3H, $8^1$-$CH_3$). MS (ESI) m/z: 653.5 ($M^+$+1).
UV-vis, $CH_2Cl_2$, $\lambda_{max}$ nm (ε): 717 (3.46×10$^4$), 655 (1.25×10$^4$), 603 (5.12×10$^3$), 516 (2.68×10$^4$), 485 (7.17×10$^3$), 456 (2.94×10$^3$), 382 (4.73×10$^4$), 355 (9.06×10$^4$).

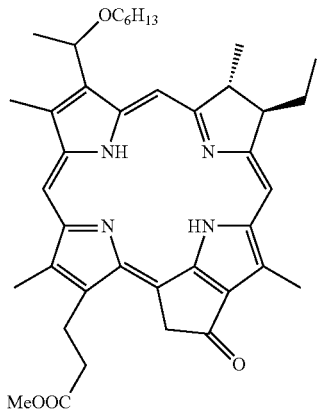

Chlorin 14: Method A (from 13): Chlorin 13 (40.0 mg, 0.0705 mmol, 1.0 equiv) was dissolved in dry $CH_2Cl_2$ (4 mL) under $N_2$. HBr gas was bulbed through the mixture for 2 min. After stirring at room temperature under $N_2$ for 5 min, the mixture was degassed and $C_6H_{13}OH$ (0.1 mL) and $K_2CO_3$ (40.0 mg) was added immediately. The resulting reaction mixture was stirred for 30 min and washed with $H_2O$ three times. Organic layer was separated, dried from $Na_2SO_4$, and evaporated to dryness. The residue was purified by flash column chromatography (silica gel, 3% acetone in $CH_2Cl_2$). Yield: 33.0 mg, 71%.

Method B (from 16): Following the procedure described for the preparation of 6, treatment of 16 (40.0 mg, 0.0705 mmol, 1.0 equiv) with $FeCl_3.6H_2O$ (66.3 mg, 4.0 equiv) resulted in the desired product. Purification was done by flash column chromatography (silica gel, 3% acetone in $CH_2Cl_2$). Yield: 25.2 mg, 55%. $^1$H NMR (400 MHz, $CDCl_3$) δ: 9.18 (s, 1H, 10-H), 9.03 (d, J=14 Hz, 1H, 5-H), 8.65 (s, 1H, 20-H), 5.79-5.86 (m, 1H, $3^1$-H), 5.48 (d, 2H, $13^2$-H), 4.41-4.50 (m, 1H, 8-H), 4.20-4.22 (m, 1H, 7-H), 3.90 (t, J=8.0 Hz, 2H, 17-$CH_2$), 3.75 (s, 3H, $COOCH_3$), 3.52-3.66 (m, 5H, $3^1$-$OCH_2$+12-$CH_3$), 3.43 (d, J=3.6 Hz, 3H, 2-$CH_3$), 3.23 (s, 3H, 18-$CH_3$), 2.94 (t, J=8.0 Hz, 2H, $17^1$-$CH_2$), 2.42-2.52 (m, 1H, $8^1$-H), 2.13-2.20 (m, 1H, $8^1$-H), 2.10 (d, J=6.8 Hz, 3H, $3^1$-$CH_3$), 1.91/1.87 (d, J=7.2 Hz, 3H, 7-$CH_3$), 1.66-1.76 (m, 3H, $3^1$-$OCH_2CH_2CH_2CH_2CH_2CH_3$), 1.15-1.23 (m, 9H, $3^1$-$OCH_2CH_2CH_2CH_2CH_2CH_3$+$8^1$-$CH_3$), 0.78-0.81 (m, 3H, $3^1$-$OCH_2CH_2CH_2CH_2CH_2CH_3$), −0.34 (br s, 1H, NH), −1.52 (br s, 1H, NH). MS (ESI) m/z: 651.4 ($M^+$+1). UV-vis, $CH_2Cl_2$, $\lambda_{max}$ nm (ε): 669 (4.45×10$^4$), 612 (6.77×10$^3$), 540 (6.77×10$^3$), 513 (1.11×10$^4$), 411 (7.82×10$^4$).

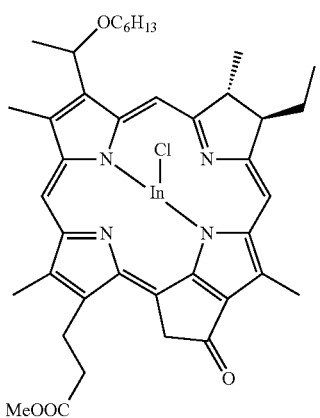

In (III) Chlorin 24: Chlorin 14 (30.0 mg, 0.046 mmol, 1.0 equiv), InCl$_3$ (50.8 mg, 5.0 equiv), K$_2$CO$_3$ (31.7 mg, 5.0 equiv) in dry toluene (10 mL) was stirred at reflux under N$_2$ for 1 hr. After cooling to room temperature, the mixture was diluted with CH$_2$Cl$_2$ (20 mL) and filtered through Celite. The solvent was washed with water three times. Organic layer was separated, dried from Na$_2$SO$_4$, and evaporated to dryness. The residue was purified by flash column chromatography (silica gel, 5% MeOH in CH$_2$Cl$_2$). Yield: 28.7 mg, 78%. $^1$H NMR (400 MHz, CDCl$_3$) δ: 9.41 (s, 1H, 10-H), 8.68/8.67 (d, 1H, 5-H), 8.54/8.33 (s, 1H, 20-H), 5.40-5.65 (m, 3H, 3$^1$-H+ 13$^1$-CH$_2$), 4.36-4.53 (m, 1H, 7-H), 4.17-4.30 (m, 1H, 8-H), 4.03 (br s, 2H, 17-CH$_2$), 3.75 (s, 3H, COOCH$_3$), 3.52/3.53 (s, 3H, 12-CH$_3$), 3.23-3.34 (m, 5H, 18-CH$_3$+O—CH$_2$), 3.01 (br s, 2H, 17$^1$-CH$_2$), 2.52 (br s, 1H, 8$^1$-H), 2.24-2.28 (m, 4H, 3$^1$-CH$_3$+8$^1$-H), 2.23 (d, J=6.8 Hz, 3H, 7-CH$_3$), 1.70-1.75 (m, 2H, 3$^1$-OCH$_2$CH$_2$CH$_2$CH$_2$CH$_2$CH$_3$), 1.18-1.32 (m, 9H, 3$^1$-OCH$_2$CH$_2$CH$_2$CH$_2$CH$_2$CH$_3$+$^{81}$-CH$_3$), 0.89-0.94 (m, 3H, 3$^1$-OCH$_2$CH$_2$CH$_2$CH$_2$CH$_2$CH$_3$. MS (ESI) m/z: 764.5 (M$^+$-Cl), 753.4 (M+-C$_6$H$_{13}$+K). UV-vis, CH$_2$Cl$_2$, λ$_{max}$ nm (ε): 660 (5.51×10$^4$), 613 (8.50×10$^3$), 570 (4.86×10$^3$), 529 (4.65×10$^3$), 429 (1.06×10$^5$).

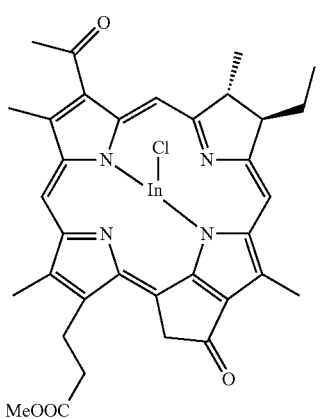

Chlorin 22: Following the procedure described for the synthesis of 24, treatment of 6 (30.0 mg, 0.0531 mmol, 1.0 equiv) with InCl$_3$ (58.8 mg, 5.0 equiv) and K$_2$CO$_3$ (36.7 mg, 5.0 equiv) resulted in the desired product. Purification was done by flash column chromatography (silica gel, 5% MeOH in CH$_2$Cl$_2$). Yield: 30.5 mg, 81%. $^1$H NMR (400 MHz, CDCl$_3$) δ: 9.68/9.67 (s, 1H, 10-H), 9.39 (s, 1H, 5-H), 8.80 (s, 1H, 20-H), 5.39-5.686 (m, 2H, 13$^1$-CH$_2$), 4.67-4.69/4.57-4.60 (m, 1H, 8-H), 4.46-4.49/4.35-4.38 (m, 1H, 7-H), 3.97-4.06 (m, 2H, 17-CH$_2$), 3.76 (s, 3H, COOCH$_3$), 3.72 (s, 3H, 12-CH$_3$), 3.56/3.57 (s, 3H, 2-CH$_3$), 3.39 (s, 3H, 18-CH$_3$), 3.21 (s, 3H, COCH$_3$), 3.02 (t, J=7.2 Hz, 2H, 17$^1$-CH$_2$), 2.40-2.60 (m, 2H, 8-CH$_2$), 2.09/1.84 (d, J=7.2 Hz, 3H, 7-H), 1.18/1.10 (t, J=7.2 Hz, 3H, 8$^1$-CH$_3$). MS (ESI) m/z: 677.4 (M$^+$-Cl). UV-vis, CH$_2$Cl$_2$, λ$_{max}$ nm (ε): 676 (5.52×10$^4$), 623 (7.76× 10$^3$), 577 (5.03×10$^3$), 532 (3.31×10$^3$), 429 (8.65×10$^4$).

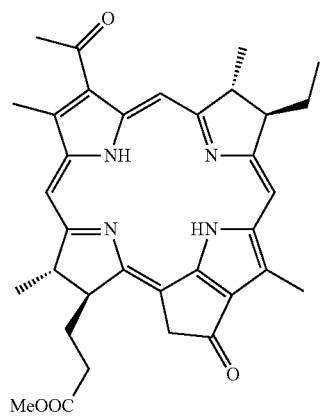 [SMILES: CC[C@H]1c2cc3[nH]c4c(c5nc(cc6[nH]c(cc(n2)[C@@H]1C)c(C(C)=O)c6C)[C@@H](C)[C@@H]5CCC(=O)OC)CC(=O)c4c3C]

Chlorin 13: Bacteriopyropheophorbide-a 11 (50.0 mg, 0.0883 mmol, 1.0 equiv) was dissolved in dichloromethane (50 mL). To this mixture was added slowly a CH$_2$Cl$_2$ (2 mL) solution of DDQ (20.0 mg, 1.0 equiv). The resulting reaction mixture was stirred at room temperature for 30 min and washed with H$_2$O three times. Organic layer was separated, dried from Na$_2$SO$_4$, and evaporated to dryness. The residue was purified by flash column chromatography (silica gel, 3% actone in CH$_2$Cl$_2$). This compound was reported by Tamiake et al. [Tamiaki, H.; Yagai, S.; Miyatake, T. Bioorg. Med. Chem. 1998, 6, 2171-2178.]. Yield: 41.0 mg, 82%. $^1$H NMR (400 MHz, CDCl$_3$) δ: 9.98 (s, 1H, 10-H), 9.57 (s, 1H, 5-H), 8.77 (s, 1H, 20-H), 5.32 (d, J=20 Hz, 1H, 13$^2$-H), 5.17 (d, J=20 Hz, 1H, 13$^2$-H), 4.56 (q, J=7.2 Hz, 1H, 18-H), 4.36-4.38 (m, 1H, 17-H), 3.69-3.74 (m, 5H, 8-CH$_2$+COOCH$_3$), 3.66 (s, 3H, 12-CH$_3$), 3.62 (s, 3H, 2-CH$_3$), 3.29 (s, 3H, 7-CH$_3$), 3.28 (s, 3H, CH$_3$CO 2.70-2.77 (m, 1H, 17$^1$-H), 2.56-2.64 (m, 1H, 17$^1$-H), 2.29-2.35 (m, 2H, 17$^1$-CH$_2$), 1.79 (d, J=7.2 Hz, 3H, 18-CH$_3$), 1.71 (t, J=7.2 Hz, 3H, 8$^1$-CH$_3$), −2.02 (s, 1H, NH). MS (ESI) m/z: 563.5 (M$^+$=1). UV-vis, CH$_2$Cl$_2$, λ$_{max}$ nm (ε): 683 (3.97×10$^4$), 623 (5.76×10$^3$), 547 (8.14×10$^3$), 515 (9.01× 10$^3$), 418 (7.63×10$^4$), 415 (5.84×10$^4$).

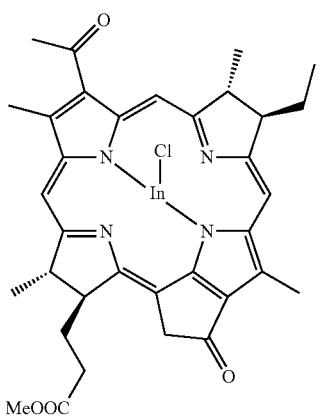

Chlorin 23: Following the procedure described for the synthesis of 24, treatment of 13 (30 mg, 0.0531 mmol, 1.0 equiv) with InCl$_3$ (58.8 mg, 5.0 equiv) and K$_2$CO$_3$ (36.7 mg, 5.0 equiv) resulted in the desired product. Purification was done by flash column chromatography (silica gel, 5% MeOH in CH$_2$Cl$_2$). Yield: 33.0 mg, 87%. $^1$H NMR (400 MHz, CDCl$_3$) δ: 10.18/10.13 (s, 1H, 10-H), 9.82/9.79 (s, 1H, 5-H), 8.78/8.70 (s, 1H, 20-H), 5.35/5.28 (d, J=20 Hz, 1H, 13$^2$-H), 5.16/5.03 (d, J=20 Hz, 1H, 13$^2$-H), 4.70/4.62 (q, J=8.0 Hz, 1H, 18-H), 4.48/4.39 (d, 1H, 17-H), 3.79-3.86 (m, 2H, 8-CH$_2$), 3.71 (t, 6H, COOCH$_3$+12-CH$_3$), 3.62/3.60 (s, 3H, 2-CH$_3$), 3.37/3.36 (s, 3H, 7-CH$_3$), 3.24 (s, 3H, CH$_3$CO), 3.44-2.87 (m, 4H, 17-CH$_2$+17$^1$-CH$_2$), 1.76 (t, 3H, 18-CH$_3$). MS (ESI) m/z: 677.3 (M$^+$-Cl). UV-vis, CH$_2$Cl$_2$, λ$_{max}$ nm (ε): 673 (4.90×10$^4$), 624 (7.89×10$^3$), 579 (4.67×10$^3$), 535 (2.69×10$^3$), 418 (7.63×10$^4$), 429 (7.80×10$^4$).

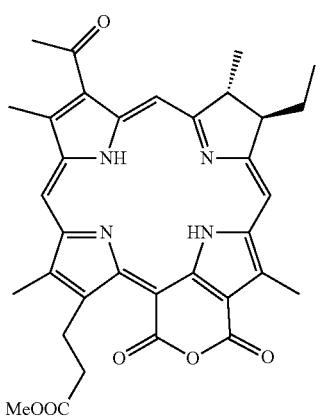 [SMILES: CC[C@H]1c2cc3[nH]c4c(c5nc(cc6[nH]c(cc(n2)[C@@H]1C)c(C(C)=O)c6C)C(C)=C5CCC(=O)OC)C(=O)OC(=O)c4c3C]

Chlorin with a fused anhydride ring 18: Following the procedure described for the preparation of 6, treatment of 17 (20.0 mg, 0.0336 mmol, 1.0 equiv) with FeCl$_3$.6H$_2$O (36.2 mg, 4.0 equiv) resulted in the desired product. Yield: 19.8 mg, 99%. $^1$H NMR (400 MHz, CDCl$_3$) δ: 9.66 (s, 1H, 10-H), 9.64 (s, 1H, 5-H), 9.01 (s, 1H, 20-H), 4.53 (q, J=6.4 Hz, 1H, 7-H), 4.43-4.36 (m, 1H, 8-H), 3.91-4.01 (m, 2H, 17-CH$_2$), 3.81 (s, 3H, COOCH$_3$), 3.77 (s, 3H, 12-CH$_3$), 3.68 (s, 3H, 2-CH$_3$), 3.29 (s, 3H, 18-CH$_3$), 3.25 (s, 3H, CH$_3$CO), 3.15 (t, J=6.0 Hz, 2H, 17$^1$-CH$_2$), 2.48-2.55 (m, 1H, 8$^1$-H), 2.13-2.21 (m, 1H, 8$^1$-H), 1.99 (d, J=7.2 Hz, 3H, 7-CH$_3$), 1.18 (t, J=7.2 Hz, 3H, 8$^1$-CH$_3$), −1.22 (br s, 1H, NH). MS (ESI) m/z: 595.3 (M$^+$+1). UV-vis, CH$_2$Cl$_2$, λ$_{max}$ nm (ε): 748 (3.73×10$^4$), 680 (5.95×10$^3$), 582 (7.05×10$^3$), 536 (3.61×10$^3$), 500 (3.96×10$^3$), 434 (8.04×10$^4$).

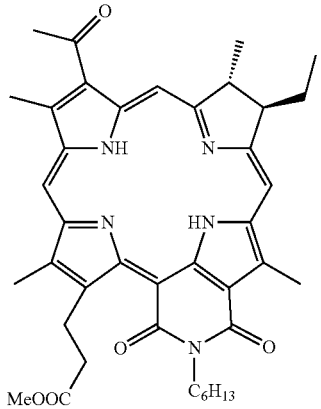

Chlorin with six member N-alkyl imide ring 20: Following the procedure described for the preparation of 6, treatment of 19 (20.0 mg, 0.023 mmol, 1.0 equiv) with FeCl$_3$.6H$_2$O (32.0 mg, 4.0 equiv) resulted in the desired product. Yield: 19.8 mg, 99%. $^1$H NMR (400 MHz, CDCl$_3$) δ: 9.52 (s, 1H, 10-H), 9.42 (s, 1H, 5-H), 8.80 (s, 1H, 20-H), 4.40 (t, J=7.2 Hz, 3H, N—CH$_2$+7-H), 4.17-4.22 (m, 1H, 8-H), 3.83-3.97 (m 2H, 17-CH$_2$), 3.74 (s, 3H, COOCH$_3$), 3.66 (s, 3H, 12-CH$_3$), 3.59 (s, 3H, 2-CH$_3$), 3.18 (s, 3H, 18-CH$_3$), 3.16 (s, 3H, CH$_3$CO), 3.07 (t, J=6.0 Hz, 2H, 17$^1$-CH$_2$), 2.38-2.44 (m, 1H, 8$^1$-H), 1.96-2.12 (m, 3H, 8$^1$-H+N—CH$_2$CH$_2$CH$_2$CH$_2$CH$_2$CH$_3$), 1.832 (d, J=7.2 Hz, 3H, 7-CH$_3$), 1.40-1.61 (m, 6H, N—CH$_2$CH$_2$CH$_2$CH$_2$CH$_2$CH$_3$), 1.10 (t, J=7.2 Hz, 3H, 8$^1$-CH$_3$), 0.94 (t, J=7.2 Hz, 3H, N—CH$_2$CH$_2$CH$_2$CH$_2$CH$_2$CH$_3$), −0.49 (br s, 2H, NH). MS (ESI) m/z: 678.6 (M$^+$+1). UV-vis, CH$_2$Cl$_2$, nm (ε): 747 (3.56×10$^4$), 678 (9.75×10$^3$), 582 (9.23×10$^3$), 503 (5.65×10$^3$), 500 (3.96×10$^3$), 440 (8.96×10$^4$).

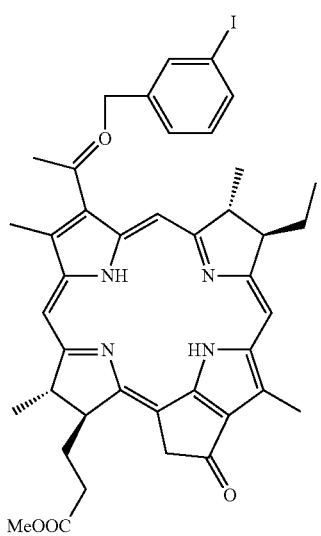

Bacteriohlorin 25: Following the procedure described for the synthesis of 16, treatment of 15 (50.0 mg, 0.0879 mmol, 1.0 equiv) with HBr gas, 3-iodobenzyl alcohol (0.1 mL), and K$_2$CO$_3$ (50.0 mg) resulted in the desired product. Purification was done by flash column chromatography (silica gel, 50% ethyl acetate in hexane). Yield: 42.8 mg, 62%. $^1$H NMR (400 MHz, CDCl$_3$) δ: 8.52 (d, J=2.4 Hz, 1H, 10-H), 8.23 (s, 1H, 5-H), 8.05 (s, 1H, 20-H), 7.73 (d, J=21.6 Hz, 1H, Ph-H), 7.62 (d, J=7.6 Hz, 1H, Ph-H), 7.26 (1H, Ph-H, overlapping with the signal of CHCl$_3$), 7.04 (t, J=8.0 Hz, 1H, Ph-H), 5.71 (q, J=6.4 Hz, 1H, 3$^1$-H), 4.97 (d, J=19.6 Hz, 1H, 13$^2$-H), 4.80 (d, J=19.6 Hz, 1H, 13$^1$-H), 4.46-4.63 (m, 2H, 3$^1$-OCH$_2$), 4.11-4.19 (m, 2H, 7-H+18-H), 4.01 (d, 1H, 17-H), 3.88-3.90 (m, 1H, 8-H), 3.62 (s, 3H, COOCH$_3$), 3.36 (s, 3H, 12-CH$_3$), 3.15 (s, 3H, 2-CH$_3$), 2.44-2.60 (m, 2H, 8$^1$-H+17$^1$-H), 2.11-2.34 (m, 3H, 17$^1$-CH$_2$+17$^1$-H), 2.04 (d, J=6.4 Hz, 4H, 3$^1$-CH$_3$+8$^1$-H), 1.65-1.77 (m, 6H, 7-CH$_3$+18-CH$_3$), 1.10-1.14 (m, 3H, 8$^1$-CH$_3$), −0.22 (s, 1H, NH). MS (ESI) m/z: 785.4 (M$^+$+1). UV-vis, CH$_2$Cl$_2$, nm (ε): 720 (3.58×10$^4$), 659 (1.21×10$^4$), 602 (4.71×10$^3$), 517 (2.55×10$^4$), 486 (6.69×10$^3$), 456 (2.81×10$^3$), 382 (4.59×10$^4$), 353 (8.63×10$^4$).

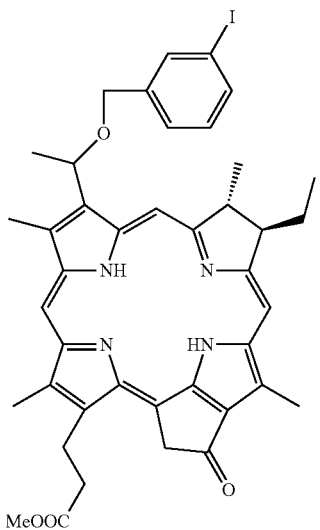 [SMILES: CC[C@H]1c2cc3[nH]c4c(c5nc(cc6[nH]c(cc(n2)[C@@H]1C)c(C(C)OCc1cccc(I)c1)c6C)C(C)=C5CCC(=O)OC)CC(=O)c4c3C]

Chlorin 8: Following the procedure described for the preparation of 6, treatment of 25 (40.0 mg, 0.051 mmol, 1.0 equiv) with FeCl$_3$.6.H$_2$O (55.1 mg, 4.0 equiv) resulted in the desired product. Purification was done by flash column chromatography (silica gel, 3% acetone in CH$_2$Cl$_2$). Yield: 20.0 mg, 50%. $^1$H NMR (400 MHz, CDCl$_3$) δ: 9.18 (s, 1H, 10-H), 9.01 (d, J=5.6 Hz, 1H, 5-H), 8.66 (s, 1H, 20-H), 7.77 (d, J=25.6 Hz, 1H, Ph-H), 7.63 (d, J=9.2 Hz, 1H, Ph-H), 7.26 (1H, Ph-H, overlapping with the signal of CHCl$_3$), 7.05 (t, J=8.0 Hz, 1H, Ph-H), 5.91 (q, J=6.8 Hz, 1H, 3$^1$-H), 5.33 (d, 2H, 13$^1$-CH$_2$), 4.52-4.69 (m, 2H, 3$^1$-OCH$_2$), 4.45-4.47 (m, 1H, 7-H), 4.23 (br s, 1H, 8-H), 3.74 (s, 5H, COOCH$_3$+17-CH$_2$), 3.55 (s, 3H, 12-CH$_3$), 3.43 (s, 3H, 2-CH$_3$), 3.18 (s, 3H, 18-CH$_3$), 2.88 (t, J=8.4 Hz, 2H, 17$^1$-CH$_2$), 2.46-2.52 (m, 1H, 8$^1$-H), 2.17 (d, J=6.8 Hz, 4H, 3$^1$-CH$_3$+8$^1$-H), 1.92/1.82 (d, J=7.6 Hz, 3H, 7-CH$_3$), 1.16-1.21 (m, 3H, 8$^1$-CH$_3$), −0.47 (br s, 1H, NH), −1.55 (br s, 1H, NH). MS (ESI) m/z: 783.4 (M$^+$+1). UV-vis, CH$_2$Cl$_2$, $\lambda_{max}$ nm (ε): 670 (4.69×10$^4$), 613 (5.54×10$^3$), 540 (5.11×10$^3$), 513 (9.57×10$^3$), 413 (7.70×10$^4$).

What is claimed is:
1. A tetrapyrrolic compound selected from the group consisting of:

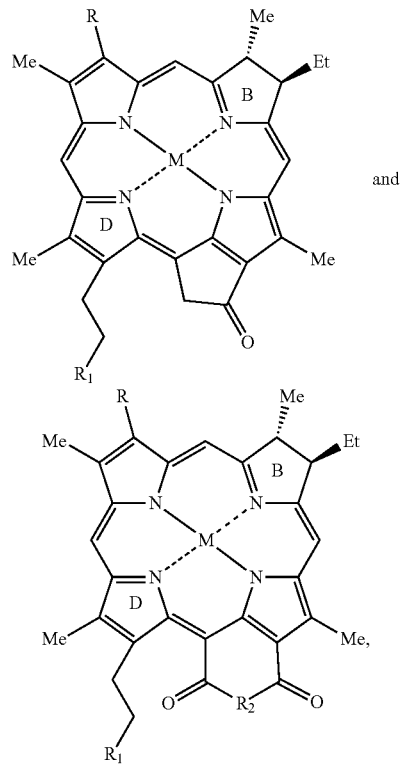

and wherein R is —COCH3 or —CH(OR$_3$)CH$_3$; where R$_3$ is a saturated or unsaturated alkyl chain with 1-8 carbon atoms, polyethylene glycol (PEG) with carbon chain of 1-8 carbon atoms, or halogen (Cl, Br, I or F)-substituted phenyl ring containing saturated or unsaturated alkyl chain with 1-8 carbon atoms as a linker or the corresponding I-124, I-125, I-131 or F-18 radionuclide;
R$_1$ is COOH or COOR$_4$ where R$_4$ is C$_{1-8}$ alkyl or substituted C$_{1-8}$ alkyl;
R$_2$ is O or N—R$_5$ where R$_5$ is C$_{1-8}$ alkyl; and
M is 2H, Ga, Pd, Al, Zn, Cu or the radioisotopes of Ga, Pd, Al, Zn, and Cu for positron emission tomography (PET) or single-photon emission computed tomography (SPEDT).
2. The compound of claim 1 having wavelength absorption in the range of 660 to 750 nm.
3. The compound of claim 1 having a purity of at least 95 percent.
4. A method of making the compound of claim 1 at over 95 percent yield by starting with a B and D ring reduced tetrapyrrolic compound and dissolving it in a halogenated hydrocarbon solvent and treating it with sufficient nitroalkane solution of FeCl$_3$6H$_2$O to oxidize the D ring and separating the resulting organic layer and drying.
5. The method of claim 4 wherein a B and D ring reduced chlorin is treated to obtain a B ring reduced -D ring oxidized chlorin.
6. The method of claim 5 where the starting tetrapyrrolic compound is methyl bacteriopyropheophorbide-a.
7. The method of claim 5 where the starting tetrapyrrolic compound is bacteriochlorophyll-a.
8. A method for imaging tumors comprising injecting a compound according to claim 1 into a subject and imaging using PET, SPECT, or fluorescence.

* * * * *